US00PP35500P2

(12) United States Plant Patent
Koning

(10) Patent No.: US PP35,500 P2
(45) Date of Patent: Nov. 21, 2023

(54) ***LAVANDULA* PLANT NAMED 'SILVER DARK ANOUK'**

(50) Latin Name: *Lavandula stoechas*
Varietal Denomination: Silver Dark Anouk

(71) Applicant: L. KONING BEHEER B.V., Nuis (NL)

(72) Inventor: Lammert Koning, Nuis (NL)

(73) Assignee: L. KONING B.V., Nuis (NL)

( * ) Notice: Subject to any disclaimer, the term of this patent is extended or adjusted under 35 U.S.C. 154(b) by 0 days.

(21) Appl. No.: 18/115,703

(22) Filed: Feb. 28, 2023

(51) Int. Cl.
*A01H 5/02* (2018.01)
*A01H 6/50* (2018.01)

(52) U.S. Cl.
USPC ..... Plt./445
CPC ..... *A01H 6/502* (2018.05)

(58) Field of Classification Search
USPC ..... Plt./445
CPC ..... A01H 6/502; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Lavandula* plant named 'Silver Dark Anouk', characterized by its compact, upright to somewhat outwardly spreading plant habit; freely branching growth habit; silvery grey-colored leaves; freely flowering habit; dark purple-colored flowers and dark purplish red-colored terminal flower bracts positioned on strong and erect peduncles; long flowering period; and good garden performance.

2 Drawing Sheets

Figure 1:
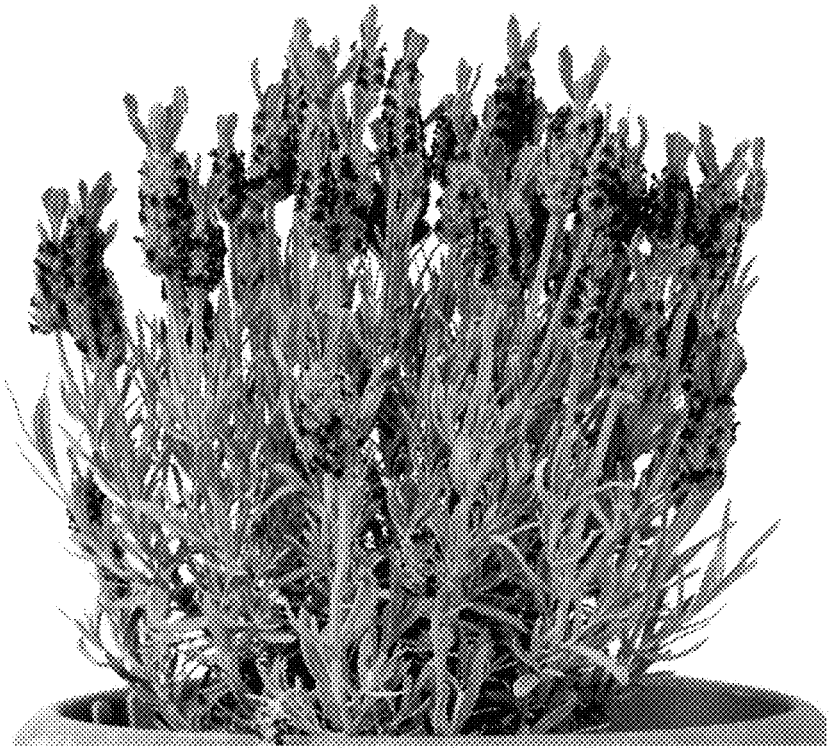

Botanical designation: *Lavandula stoechas.*
Cultivar denomination: 'SILVER DARK ANOUK'.

STATEMENT REGARDING PRIOR DISCLOSURES BY APPLICANT

An European Plant Breeder's Rights application for the instant plant was filed by the Applicant on Jun. 30, 2022, application number 2022/1625. Foreign priority is not claimed to this application.

BACKGROUND OF THE INVENTION

The present invention relates to a new and distinct *Lavandula* plant, botanically known as *Lavandula stoechas*, commonly referred to as Lavender and hereinafter referred to by the name 'Silver Dark Anouk'.

The new *Lavandula* plant is a product of a planned breeding program conducted by the Inventor in Boskoop, The Netherlands. The objective of the breeding program was to develop new unique *Lavandula* plants with good performance and attractive plant fotm and flower coloration.

The new *Lavandula* is a naturally-occurring branch mutation of 'Anouk Deluxe 173', disclosed in U.S. Plant Pat. No. 28,850. The new *Lavandula* plant was discovered and selected by the Inventor on a single flowering plant from within a large population of plants of 'Anouk Deluxe 173' in a controlled environment in Boskoop, The Netherlands in 2018.

Asexual reproduction of the new *Lavandula* plant by terminal cuttings in a controlled greenhouse environment in Boskoop, The Netherlands since September, 2018 has shown that the unique features of this new *Lavandula* plant are stable and reproduced true to type in successive generations.

SUMMARY OF THE INVENTION

Plants of the new *Lavandula* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of the new *Lavandula* plant. These characteristics in combination distinguish 'Silver Dark Anouk' as a new and distinct *Lavandula* plant:

1. Compact, upright to somewhat outwardly spreading plant habit.
2. Freely branching growth habit.
3. Silvery grey-colored leaves.
4. Freely flowering habit.
5. Dark purple-colored flowers and dark purplish red-colored terminal flower bracts positioned on strong and erect peduncles.
6. Long flowering period.
7. Good garden performance.

Plants of the new *Lavandula* differ primarily from plants of the mutation parent, 'Anouk Deluxe 173', primarily in leaf color as plants have silvery grey-colored leaves whereas plants of 'Anouk Deluxe 173' have greyish green-colored leaves.

Plants of the new *Lavandula* can be compared to plants of the *Lavandula stoechas* 'Silver Anouk', disclosed in U.S. Plant Pat. No. 20,068. In side-by-side comparisons, plants of the new *Lavandula* differ primarily from plants of 'Silver Anouk' in the following characteristics:

1. Plants of the new *Lavandula* are more compact and more upright than plants of 'Silver Anouk'.
2. Plants of the new *Lavandula* have darker purplish red-colored terminal flower bracts than plants of 'Silver Anouk'.
3. Plants of the new *Lavandula* will rebloom whereas plants of 'Silver Anouk Deluxe' rarely rebloom.

Plants of the new *Lavandula* can also be compared to plants of the *Lavandula stoechas* 'Anouk Deluxe 169', disclosed in U.S. Plant Pat. No. 28,851. In side-by-side comparisons, plants of the new *Lavandula* differ primarily from plants of 'Anouk Deluxe 169' in the following characteristics:

1. Plants of the new *Lavandula* have silvery grey-colored leaves whereas plants of 'Anouk Deluxe 169' have greyish green-colored leaves.
2. Plants of the new *Lavandula* have dark purplish red-colored terminal flower bracts whereas plants of 'Anouk Deluxe 169' have red purple to purple-colored terminal flower bracts.
3. Plants of the new *Lavandula* will rebloom whereas plants of 'Anouk Deluxe 169' rarely rebloom.

BRIEF DESCRIPTION OF THE PHOTOGRAPHS

The accompanying photographs illustrate the overall appearance of the new *Lavandula* plant showing the colors as true as it is reasonably possible to obtain in colored reproductions of this type. Colors in the photographs may differ slightly from the color values cited in the detailed botanical description which accurately describe the colors of the new *Lavandula* plant.

The photograph on the first sheet (FIG. 1) is a side perspective view of a typical flowering plant of 'Silver Dark Anouk' grown in a container.

Figure 2:
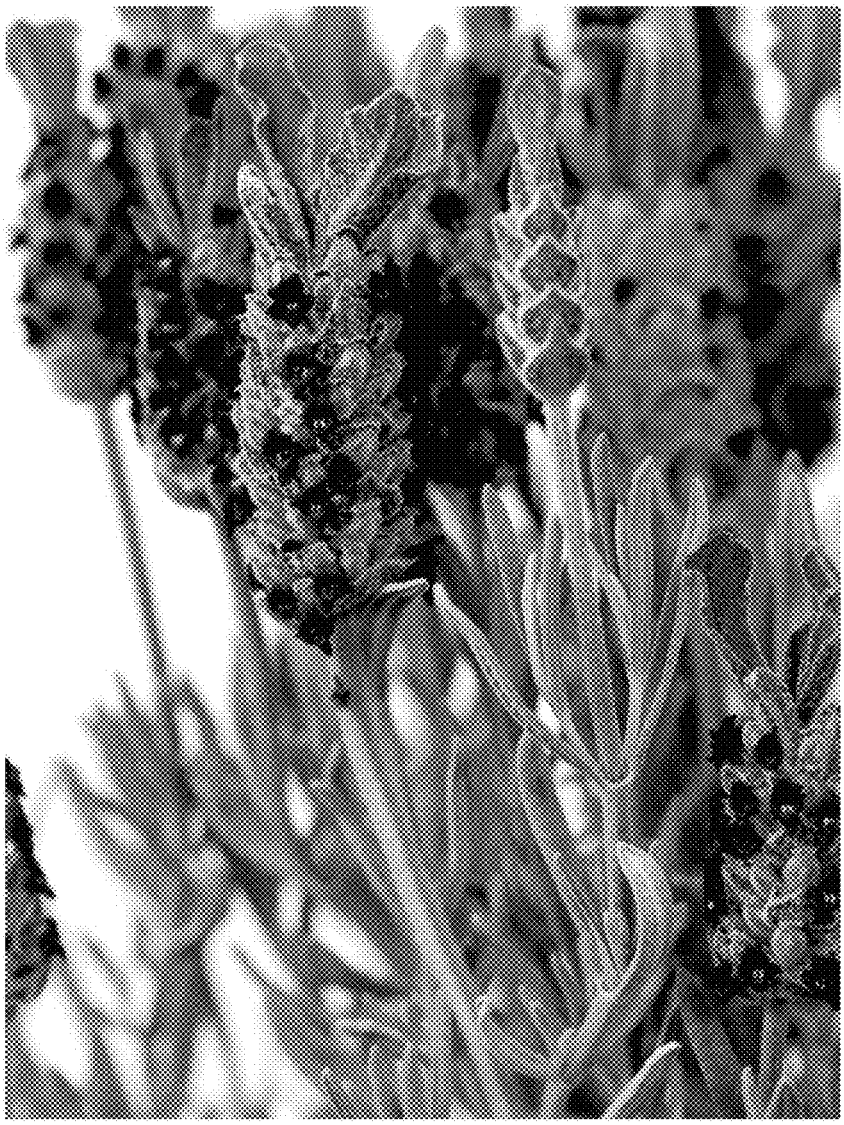

The photograph on the second sheet (FIG. 2) is a close-up view of a typical flowering plant of 'Silver Dark Anouk'.

DETAILED BOTANICAL DESCRIPTION

Plants used in the aforementioned photographs and following detailed description were grown in 22-cm containers during the spring and early summer in an outdoor nursery in Boskoop, The Netherlands and under cultural practices typical of commercial *Lavandula* production. Plants were pinched one time and were ten months old when the photographs and description were taken. During the production of the plants, day temperatures ranged from 10C to 30C and night temperatures ranged from 5C to 20C. In the following description, color references are made to The Royal Horticultural Society Colour Chart, 2015 Edition, except where general tetms of ordinary dictionary significance are used.

Botanical classification: *Lavandula stoechas* 'Silver Dark Anouk'.

Parentage: Naturally-occurring branch mutation of 'Anouk Deluxe 173', disclosed in U.S. Plant Pat. No. 28,850.

Propagation:

*Type.*—Terminal vegetative cuttings.

*Time to initiate roots, summer and winter.*—About ten days at temperatures about 18C.

*Time to produce a rooted young plant, summer.*—About 60 days at temperatures about 20C.

*Time to produce a rooted young plant, winter.*—About 70 days at temperatures about 20C.

*Root description.*—Fine, fibrous; initially white in color and becoming more brown with development; actual color of the roots is dependent on substrate composition, water quality, fertilizer type and fotmulation.

*Rooting habit.*—Freely branching; dense.

Plant description:

*Plant and growth habit.*—Herbaceous perennial; compact, upright to somewhat outwardly spreading plant habit; flattened globular in overall plant shape; freely branching habit; moderately vigorous growth habit; moderate growth rate; flowers arranged in verticillasters on crowded spikes with showy terminal flower bracts.

*Plant height, soil level to top of foliar plane.*—About 20.2 cm.

*Plant height, soil level to top of floral plane.*—About 26.1 cm.

*Plant width.*—About 25.6 cm.

*Lateral branch description.*—Quantity per plant: About 32 primary lateral branches each with about two or three secondary lateral branches developing per plant; pinching enhances branching potential. Length: About 9.9 cm. Diameter: About 2.5 mm. Internode length: About 1.5 cm. Strength: Moderately strong. Aspect: Primary lateral branches, upright to about 40 degrees from vertical; secondary lateral branches, about 35 degrees from primary lateral branch axis. Texture and luster: Densely tomentose; matte. Color, when developing: Close to 145B. Color, developed: Close to 146D densely covered with tomentose pubescence, close to 193A to 193B; with development, close to 199B and N199C.

*Leaf description.*—Arrangement: Opposite, simple; sessile. Length: About 3.1 cm. Width: About 6 mm. Shape: Oblanceolate to narrowly oblong. Apex: Acute. Base: Cuneate. Margin: Entire; moderately revolute; not lobed. Texture and luster, upper surface: Densely tomentose; not rugose; matte. Texture and luster, lower surface: Densely tomentose; slightly rugose; matte. Fragrance: Strongly aromatic, pungent. Venation pattern: Pinnate. Color: Developing leaves, upper surface: Close to 138B. Developing leaves, lower surface: Close to 138C. Fully expanded leaves, upper surface: Close to 191A; venation, close to 193B. Fully expanded leaves, lower surface: Close to 191B; venation, close to 192B.

Flower description:

*Flower type, arrangement and habit.*—Small single salverform flowers arranged in compact verticillasters on crowded terminal spikes; freely flowering, about 100 flowers developing per inflorescence and about 6,000 flowers developing per plant; flowers with two-lobed upper lip and three-lobed lower lip; flowers face mostly outwardly on the spike; inflorescences with showy terminal flower bracts.

*Natural flowering season.*—Long flowering period; continuous from late spring into the summer in The Netherlands; plants reblooming for about ten weeks.

*Flower longevity on the plant.*—Individual flowers last about four weeks on the plant; flowers not persistent.

*Fragrance.*—None detected.

*Flower buds.*—Length: About 7 mm. Diameter: About 1.75 mm. Shape: Oblong. Texture and luster: Densely tomentose; matte. Color: Close to 200A; proximally, close to 145B.

*Inflorescence size.*—Height, including terminal flower bracts: About 5.1 cm. Height, excluding terminal flower bracts: About 3.2 cm. Diameter, at terminal flower bracts: About 2.1 cm. Diameter, below flower bracts: About 1.8 cm.

*Flower size.*—Diameter: About 4 mm by 4.5 mm. Depth (height): About 9 mm. Throat diameter: About 1 mm. Tube length: About 6 mm. Tube diameter: About 1.1 mm.

*Petals.*—Quantity and arrangement: Upper lip, two-lobed and lower lip, three-lobed. Length, upper lip: About 2 mm. Length, lower lip: About 1.5 mm. Width, upper lip: About 1.5 mm. Width, lower lip: About 1 mm. Shape: Roughly spatulate; lower 75% fused into a tube. Apex: Obtuse. Margin: Entire; moderately undulate. Texture and luster, upper surface: Smooth, glabrous; moderately velvety; not rugose; matte. Texture and luster, lower surface: Smooth, glabrous; slightly velvety; not rugose; matte. Texture, throat: Smooth, glabrous; slightly velvety. Texture, tube: Smooth, glabrous. Color: When opening, upper and lower surfaces: Close to N186B. Fully opened, upper and lower surfaces: Close to N186B; venation, close to N186B; color does not change with subsequent development. Throat: Close to N92A; venation, close to N92A. Tube: Close to 86A fading proximally to close to 85D; venation, claose to 86A and 85D.

*Terminal flower bracts.*—Quantity and arrangement: About four to six positioned mostly upright at inflorescence apex. Length: About 2 cm. Width: About 6.5 mm. Shape: Obovate to oblanceolate; slightly to moderately concave. Apex: Bluntly acute. Base: Narrowly acuminate. Margin: Entire; moderately undulate. Texture and luster, upper surface: Sparsely tomentose; matte. Texture and luster, lower surface: Densely tomentose; matte. Color, upper surface: Close to a blend of N77A and N77B; midvein, close to 200A. Color, lower surface: Close to N77A; midvein, close to 200A.

*Basal flower bracts.*—Quantity and arrangement: Each group of five flowers is subtended by a single basal flower bract. Length: About 9 mm. Width: About 8 mm. Shape: Broadly rhomboidal. Apex: Abruptly acute. Base: Acuminate. Margin: Entire to irregularly ciliate. Texture and luster, upper surface: Moderately tomentose; slightly glossy. Texture and luster, lower surface: Densely tomentose; matte. Color, upper surface: Close to 200C; venation, close to 146A and 147B. Color, lower surface: Close to N186C; venation, close to 200A.

*Sepals.*—Quantity and arrangement: Five, fused into a campanulate tube. Calyx length: About 5 mm. Calyx diameter: About 2 mm. Length: About 5 mm. Width: About 0.75 mm. Shape: Linear. Apex: Acute. Margin: Entire. Texture and luster, upper surface: Smooth, glabrous; glossy. Texture and luster, lower surface: Densely tomentose; matte. Color: When opening and fully opened, upper surface: Close to 147C and apex, close to 200A; venation, close to 183A. When opening and fully opened, lower surface: Close to 145A and distally, close to N186C.

*Peduncles.*—Length: About 6.7 cm. Diameter: About 2 mm. Aspect: Mostly upright. Strength: Strong. Texture and luster: Densely tomentose; matte. Color: Close to 146B and 193A.

*Reproductive organs.*—Stamens: Quantity per flower: Four. Filament length: About 1 mm. Filament color: Close to 86B. Anther shape: Short oblong; dorsifixed. Anther size: About 0.75 mm by 0.75 mm. Anther color: Close to 161D. Pollen amount: Scarce. Pollen color: Close to 16B. Pistils: Quantity per flower: One. Pistil length: About 4 mm. Stigma shape: Club-shaped. Stigma diameter: About 0.3 mm. Stigma color: Close to N186B. Style length: About 3.7 mm. Style color: Close to 85C. Ovary color: Close to 146C.

*Seeds and fruits.*—To date, seed and fruit production has not been observed on plants of the new *Lavandula.*

Pathogen & pest resistance: To date, plants of the new *Lavandula* have not been noted to be resistant to pathogens and pests common to *Lavandula* plants.

Garden performance: Plants of the new *Lavandula* have exhibited good tolerance to rain and wind and have been observed to tolerate temperatures from about 1C to about 40C and to be suitable for USDA Hardiness Zones 7 to 10.

It is claimed:

1. A new and distinct *Lavandula* plant named 'Silver Dark Anouk' as illustrated and described.

* * * * *